United States Patent [19]

Shimonaka

[11] 4,326,531
[45] Apr. 27, 1982

[54] DEVICE FOR OPERATING A COELIAC TUBULAR MEMBER-CLOSING IMPLEMENT

[75] Inventor: Hideki Shimonaka, Hachioji, Japan

[73] Assignee: Olympus Optical Co., Ltd., Tokyo, Japan

[21] Appl. No.: 76,321

[22] Filed: Sep. 17, 1979

[30] Foreign Application Priority Data

Sep. 20, 1978 [JP] Japan .................................. 53-115693

[51] Int. Cl.$^3$ ............................................ A61B 17/12
[52] U.S. Cl. ..................................................... 128/326
[58] Field of Search .................. 128/325, 326, 303 R, 128/321, 330, 334 R, 334 C, 335; 24/16 PB, 3 M, 143 B, 17 A, 73 PB, 150 FP

[56] References Cited

U.S. PATENT DOCUMENTS 3,636,594 1/1972 Faivre .......................... 24/143 B X
3,958,576 5/1976 Komiya ............................. 128/346
4,060,089 11/1977 Noiles ........................ 128/334 C X

FOREIGN PATENT DOCUMENTS 53-38185 4/1978 Japan .............................. 128/303 A

*Primary Examiner*—Michael H. Thaler

[57] ABSTRACT

A device for operating the coeliac tubular member-closing implement comprises an outer tube, a hollow cylindrical needle which is inserted into the outer tube and whose forward end portion contains the coeliac tubular member-closing implement, a push tube for forcing the coeliac tubular member-closing implement out of the needle, a drive tube which is inserted into the push tube to move a second stop toward a first stop, and an elongated holding member which is inserted into the drive tube to hold the coeliac tubular member-closing element at the prescribed position. The needle is let to penetrate the coeliac tubular member which is going to be closed, with the coeliac tubular member-closing implement received in the needle. Thereafter, the needle is pulled out by the push tube with the coeliac tubular member-closing implement still retained in the coeliac tubular member. The second stop is pushed by the drive tube, thereby closing the coeliac tubular member by the action of both first and second stops.

4 Claims, 26 Drawing Figures

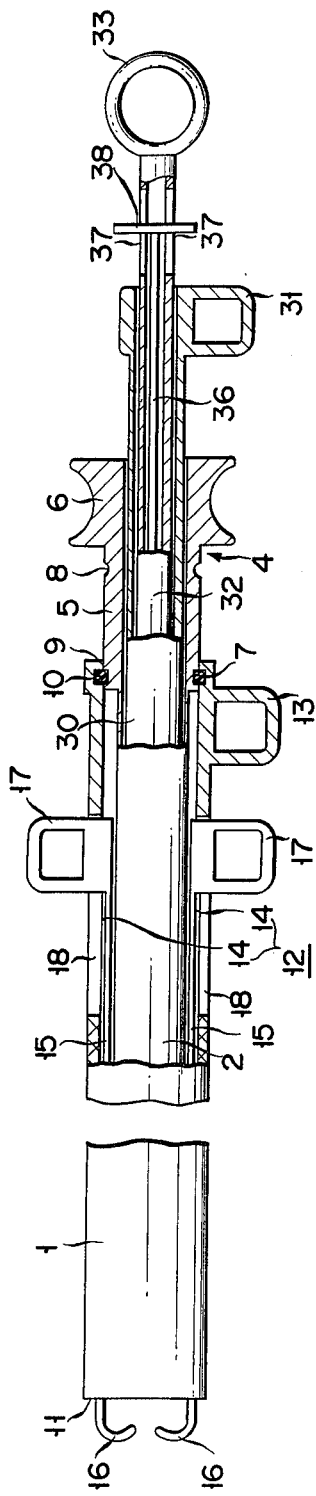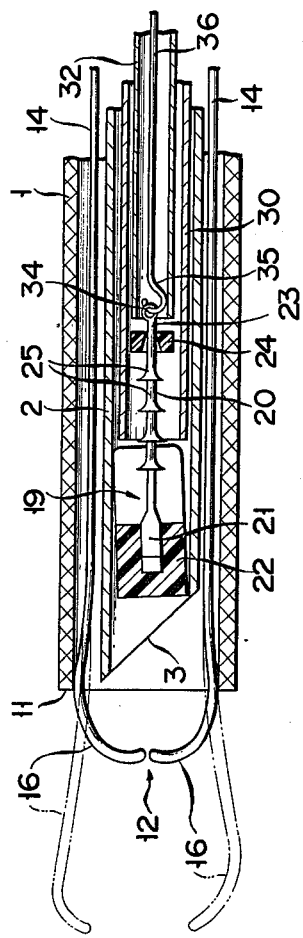

DEVICE FOR OPERATING A COELIAC TUBULAR MEMBER-CLOSING IMPLEMENT

BACKGROUND OF THE INVENTION

This invention relates to an implement for closing a tubular member of the coeliac cavity such as a uterine tube, and a device for operating said implement.

The customary practice of closing the tubular member of the coeliac cavity such as the uterine tube is to fold the tubular member and insert the folded portions of tubular member into a ring. However, this customary practice has the drawbacks that as time goes on, the ring falls off the folded tubular member due to a tensile force applied to the tubular member or the movement of the coeliac tissue, thus leading to the failure to close the tubular member. Further, an attempt to fasten the ring more tightly on the tubular member obstructs the blood passage through that portion of the tubular member which is forcefully tightened by the ring, probably leading to the destruction or rottenness of said portion. Even the removal of the ring before the occurrence of such worst condition often results in the failure to restore the physiological function of the tightly fastened tubular member.

SUMMARY OF THE INVENTION

An object of this invention is to provide an implement which can permanently and reliably close a tubular member of the coeliac cavity such as a uterine tube without the obstruction of the blood passage through the closed portion of the tubular member and consequently the decrease and rottenness of the tightly fastened portion of the tubular member, and a device for operating said closing implement.

To attain the above-mentioned object, this invention provides an implement for closing the tubular member of the coeliac cavity which comprises a penetrating member through which a plurality of linearly arranged fructoconical engagement members whose diameter progressively increases toward one end of the penetrating member, a first stop fixed to said one end portion of the penetrating member, and a second stop provided with a fructoconical hole whose diameter progressively increases toward said one end of the penetrating member, the other end portion of which inserted into said fructoconical hole.

A device for operating the tubular member-closing implement of this invention comprises an elongated rigid or flexible outer tube, a hollow cylindrical needle for holding the tubular member-closing implement in the distal end portion, a forceps member provided with hook means reciprocably set between the outer tube and needle and arranged to protrude from the distal end of the outer tube to hold the coeliac tubular member, means for pushing the tubular member-closing implement from the distal end of the outer tube to close said implement, and means for holding said tubular member-closing implement.

The means of this invention for holding the tubular member-closing implement ensures the easy and reliable operation of said closing implement.

The tubular member-closing implement properly closes the tubular member of the coeliac body without the decrease or any other difficulties of the closed tubular member.

BRIEF DESCRIPTION OF THE DRAWING

This invention can be fully understood from the following detailed description with reference to the accompanying drawings in which:

FIG. 1 is a partly exploded side view of a coeliac tubular member-closing implement according to an embodiment of this invention;

FIG. 2 is a longitudinal sectional view of the distal end portion of FIG. 1;

DETAILED DESCRIPTION OF THE PREFERRED EMBODIMENTS

Figure 3:
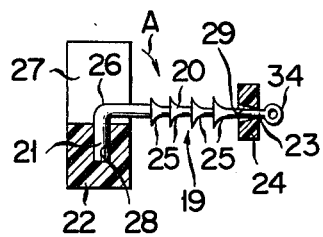
FIG. 3 is a side view of the tubular member-closing implement embodying the invention.

The implement of this invention for closing a coeliac tubular member is applicable to any form of the coeliac tubular member particularly in a human body, for briefness however, the following description only refers to the case where the coeliac tubular member-closing implement is applied to the closing of a uterine tube in particular.

Referring to FIGS. 1 and 2, the coeliac tubular member-closing implement (simply referred to as "the closing implement") of this invention comprises an elongated rigid or flexible outer tube 1 (in case of a flexible tube, it is formed of, for example, a set tube), and a hollow cylindrical stainless steel needle 2 arranged to reciprocate through the rigid or flexible outer tube 1. The forward end portion of the needle 2 is cut slantwise to provide a sharp tip. The rear end portion 4 of the needle 2 comprises a sleeve section 5 and a terminal knob 6. The sleeve section 5 has an outer diameter substantially equal to the inner diameter of the outer tube 1 so that the sleeve section 5 is slidable along the inner face of the outer tube 1. Annular grooves 7, 8 are respectively formed in the outer surface of the forward and rear end portions of the sleeve section 5. The annular grooves 7, 8 selectively engage an O ring 10 provided on the inner face of the proximal end 9 of the outer tube 1. As illustrated in FIG. 1, while the front annular groove 7 engages the O-ring 10, the forward end portion 3 of the needle 2 remains retracted into the outer tube 1. When the terminal knob 6 is manually pushed until the rear annular groove 8 engages the O ring 10, the forward end portion 3 of the needle 2 is most protruded from the distal end 11 of the outer tube 1. A handle 13 is provided on the lateral wall of the proximal end portion of the outer tube 1.

The closing device comprises a forceps 12. According to the first embodiment of FIGS. 1 and 2, the forceps 12 comprises a pair of forceps members 14 facing each other across the needle 2. Each forceps member 14 comprises a stem section 15 extending lengthwise of the outer tube 1 between the outer tube 1 and needle 2, a two-pronged hook section 16 disposed at the forward end portion of the stem section 15, and a handle 17 radially protruding outward from the proximal end portion of the outer tube 1. The two prongs of each hook section 16 are normally elastically urged outward radially of the outer tube 1, bent inward radially thereof, and spaced from each other at a distance longer than the outer diameter of the needle 2. A pair of slots 18 extending lengthwise of the outer tube 1 are provided in that portion of the lateral wall of the outer tube 1 which is positioned nearer to the proximal end 9 of the outer tube 1. The respective handles 17 protrude from the corresponding slots 18 to the outside of the outer tube 1. The manual operation of the handles 17 of the forceps members 14 causes the hood sections 16 to be retracted into the outer tube 1 as indicated in solid lines in FIG. 2 or to be pushed out from the distal end 11 of the outer tube 1 as shown in the broken lines in FIG. 2. When the hook sections 16 of the forceps members 14 are protruded, a space between the mutually facing hook sections 16 of the forceps members 14 is broadened wider than the diameter of the uterine tube due to the elastic force of the hook sections 16.

A coeliac tubular member-closing implement 19 received in the forward end portion of the needle 2 comprises, as shown in FIGS. 2 and 3, a penetrating member 20, a first stop 22 fixed to the forward end portion 21 of the penetrating member 20 and a ring-shaped second stop 24 mounted on the rear end portion 23 of the penetrating member 20.

Figure 4:
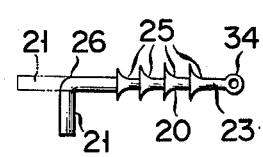
FIG. 4 shows the action of the penetrating member of FIG. 3.

The penetrating member 20 is prepared from synthetic resin such as polytetrafluoroethylene which is anticorrosive, harmless to the uterine tube and elastic. The intermediate part of the penetrating member 20 between both end portions 21, 23 is formed, as shown in FIGS. 2 and 4, of linearly connected frustoconical engagement members 25 whose diameter progressively increases toward the forward end portion 21. As seen from FIG. 4, the forward end portion 21 is bent at a point 26 perpendicularly to the intermediate part. The forward end portion 21 is cylindrical, and is raised elastically in alignment with the intermediate part as indicated in the chain lines in FIG. 4, when subjected to an external force.

Figure 5:
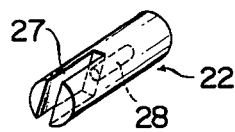
FIG. 5 is an oblique view of a first stop embodying the invention.
Figure 6:
FIG. 6 is a longitudinal sectional view of a second stop embodying the invention.
Figure 7:
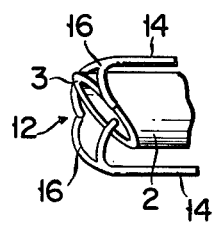
FIG. 7 indicates the state in which a needle is being pushed forward in the embodiment of FIGS. 1 and 2.
Figure 8:
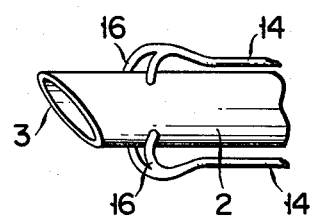
FIG. 8 shows the state in which a needle is being protruded in the embodiment of FIG. 7.

The first stop 22 is prepared from synthetic resin such as silicone resin or polytetrafluoroethylene which is anticorrosive and harmless to the uterine tube. As best shown in FIG. 5, the first stop 22 is a columnar member provided with a slot 27 extending lengthwise from one end to the center. An elongated hole 28 is provided which extends from the bottom wall of the slot 27 to the other end of the first stop 22. The forward end portion 21 of the penetrating member 20 is fixedly inserted into the elongated hole 28.

The second stop 24 is formed of a ring member prepared from synthetic resin such as silicone resin or polytetrafluoroethylene which is anticorrosive, harmless to the uterine and elastic. The second stop 24 is provided with a concentric penetrating bore 29 which has a complementalry shape to that of the respective linearly connected frustoconical engagement members 25, that is, whose diameter progressively increases toward the forward end portion 21 of the penetrating member 20. The rear end portion 23 of the penetrating member 20 is inserted into the penetrating bore 29.

Inserted into the needle 2 is a push tube 30 which has a smaller outer diameter than that of the first stop 22, and is used to force the first stop 22 outward. A handle 31 (FIG. 1) is formed on the lateral outer surface of the rear end portion of the push tube 30. Inserted into the push tube 30 is a drive tube 32 which has a smaller outer diameter than that of the second stop 24 and is used to push the second stop 24 as described later. A ring-shaped handle 33 (FIG. 1) is provided on the rear end of the drive tube 32. An elongated holding member or rod 36 is inserted into the drive tube 32 to support the penetrating member 20. As shown in FIG. 2, the holding member 36 has a hook 35 engaging a ring 34 formed at the rear end of the penetrating member 20. A handle 38 is fixed at right angles to the holding member 36. The handle 38 protrudes from the drive tube 32 through a pair of slits 37, which are formed on the lateral wall of the rear end portion of the drive tube 32 to extend axially thereof in a state crosswise spaced from each other.

When the closing implement 19 is pulled into the forward end portion of the needle 2 with the hook 35 of the holding member 36 engaged with the ring 34 of the closing implement 19, the first stop 22 is rotated by the inner face of the forward end portion of the needle 2 in the direction of an arrow A indicated in FIG. 3. Therefore, the forward bent portion 21 of the penetrating member 20 is straightened as shown in the chain lines in FIG. 4. Then, the first stop 22 is set in the forward end portion of the needle 2 in a state indicated in FIG. 2.

Figure 9:
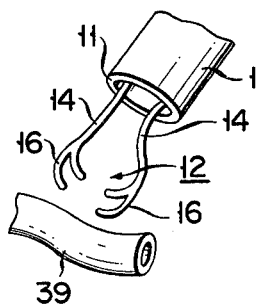
FIG. 9 indicates the state in which a pair of forceps elements of FIGS. 1 and 2 are pushed out of the outer tube to be drawn near the uterine tube.
Figure 10:
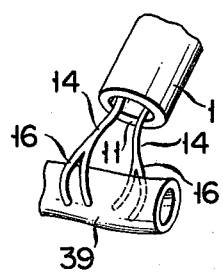
FIG. 10 shows the state in which a pair of forceps elements of FIGS. 1 and 2 have gripped the uterine tube.

In operation, the closing device with a closing implement 19 disposed in the needle 2 is inserted into the channel of an endoscope such as a laparoscope introduced into the coeliac cavity, while, as shown in FIG. 1, the forceps members 12, needle 2, push tube 30 and drive tube 32 are retracted most backward, and the holding member 36 is so moved as to cause the handle 38 to be set at the middle of the slits 37. When the distal end 11 of the outer tube 1 is drawn near, as shown in FIG. 9, to a uterine tube 39 which is to be closed, the handles 17 of the forceps members 14 are pushed toward the distal end 11 of the outer tube 1. As a result, the hooks 16 of the forceps members 14 are forced out of the outer tube 1 to be separated from each other more widely. Thereafter, the handle 13 of the outer tube 1 is pushed to let the distal end 11 of the outer tube 1 be drawn near the uterine tube 39 with the forceps members 14 unmoved. The hooks 16 clamp the uterine tube 39 therebetween. When the handles 17 are pulled slightly backward, the uterine tube 39 are tightly gripped by the hooks 16.

Figure 11:
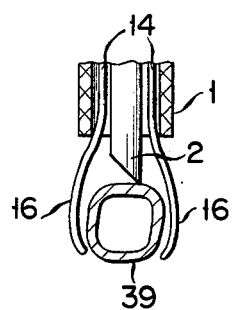
FIG. 11 shows the state in which the needle of FIGS. 1 and 2 is being protruded.
Figure 12:
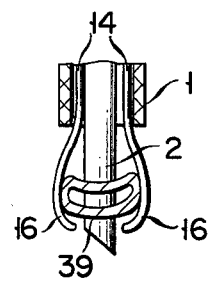
FIG. 12 indicates the state in which the needle of FIGS. 1 and 2 has pierced the uterine tube.
Figure 13:
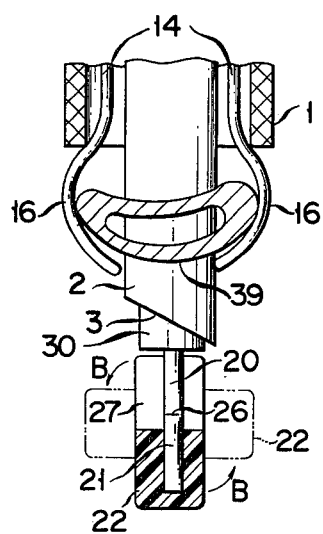
FIG. 13 shows the state in which the first stop has been pushed out of the forward end of the needle which has pierced the uterine tube.

Thereafter, the handle 6 of the needle 2 is pushed to drive the needle 2 forward until the annular groove 8 engages the O-ring 10. After the needle 2 is brought to the position indicated in FIG. 11, the forward end 3 of the needle 2 penetrates the uterine tube 39. The handle 31 is pushed to let the first stop 22 be fully forced out of the forward end 3 of the needle 2 by the forward end of the push tube 30. The pushed first stop 22 is rotated in the direction of an arrow B indicated in FIG. 13 by the righting moment of the forward end portion 21 of the penetrating member 20 to be brought to a position shown in the chain lines.

Figure 14:
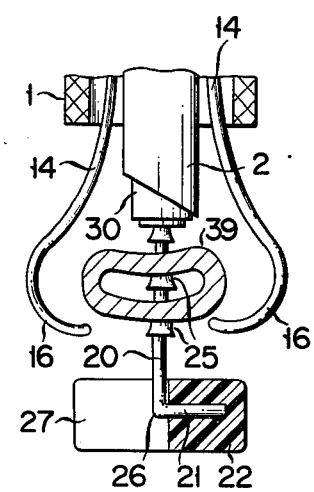
FIG. 14 indicates the state in which the needle has been pulled out of the uterine tube.
Figure 15:
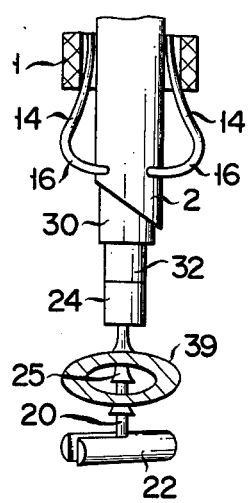
FIG. 15 shows the state in which the second stop is being moved forward the first stop with the uterine tube set therebetween.
Figure 16:
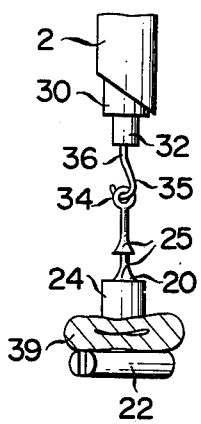
FIG. 16 illustrates the state in which the uterine tube is tightly closed by the action of the first and second stops.

When the knob 38 is moved by the fingers to pull back the outer tube 1, needle 2 and push tube 30 with care taken to keep the holding member 36 unmoved, the penetrating member 20 passes through the uterine tube 39. At this time, the hooks 16 are separated from each other more widely to release the uterine tube 39 (FIG. 14). Thereafter as shown in FIG. 15, the outer tube 1, forceps 12, needle 2, and push tube 30 are retracted. The handle 38 is pushed to cause the second stop 24 to be driven toward the first stop 22 by the forward end of the push tube 32. As the frustoconical bore 29 of the second stop 24 passes over the linearly connected frustoconical engagement members 25 in succession, the second stop 24 is brought closer to the first stop 22. The uterine tube 39 is tightly compressed by the action of both stops 22, 24. The movement of the second stop 24 toward the first stop 22 fully closes the uterine tube 39. However, this movement is continued only to such an extent that the blood passage through the closed uterine tube 39 is not obstructed.

When the second stop 24 passes over one of the frustoconical engagement members 25 the end face of the second stop at which the smaller diameter end of the similarly frustoconical bore 29 opens is in contact with the bottom wall of the base of the frustoconical engagement member 25. Where, therefore, a force is even applied to the second stop 24 to let it separate from the first stop 22, the second stop 24 can not easily get over those of the frustoconical engagement members 25 which have already been passed over by the second stop 24. Consequently, the uterine tube 39, once closed, is little likely to be opened again.

Figure 17:
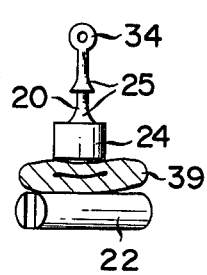
FIG. 17 shows the state of the uterine tube-closing implement, in which the uterine tube has been closed by the action of the first and second stops of the penetrating member.

When the above-mentioned closure of the uterine tube 39 is brought to an end, the respective movable members of the closing implement (except for the holding member 36) are retracted to the position shown in FIG. 1. As a result, the ring 34 of the penetrating member 20 and the hook 35 of the holding member 36 protrude from the distal end 11 of the outer tube 1. Thereafter, the handle 33 is pushed to move forward only the holding member 36. The hook 35 is removed from the ring 34 as shown in FIG. 17. The closing device, together with the endoscope, is pulled out of the coeliac cavity, thus completing the operation of closing the uterine tube 39.

Figure 18:
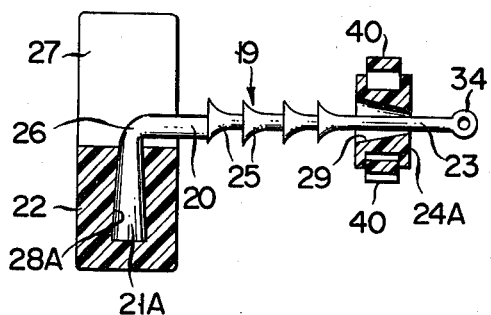
FIG. 18 is a longitudinal sectional view of a uterine tube-closing implement according to a second embodiment of the invention.
Figure 19:
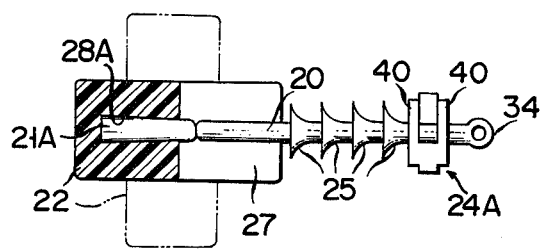
FIG. 19 shows the action of the uterine tube-closing implement according to said second embodiment of FIG. 18.
Figure 20:
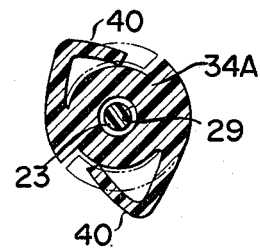
FIG. 20 is a cross sectional view of the second stop of FIG. 18.

FIGS. 18 to 20 illustrate a coeliac tubular member-closing implement according to a second embodiment of this invention. A second stop 24A mounted on the rear end 23 of a penetrating member 20 is prepared from the same material as the second stop 24 of the first embodiment. A pair of V-shaped arms 40 are formed on the peripheral surface of the second stop 24A to protrude radially. When the second stop 24A is left free, the V-shaped arms 40 radially protrude from the second stop 24A, thereby enabling the second stop 24A to touch the uterine tube 39 in a broader area, and consequently elevating the efficiency of closing the uterine tube 39. When the second stop 24A is inserted into the forward end portion of the needle 2, the space between the V-shaped arms 40 is shortened by the inner surface of the needle 2. Consequently, the second stop 24A as a whole is reduced in size, making it unnecessary to particularly increase the diameter of the needle 2.

The forward end portion 21A of the penetrating member 20 is shaped like a frustoconical form whose diameter progressively increases toward its free end. The hole 28A of a first stop 22 is shaped like a frustoconical form complementary to the forward end portion 21A of the penetrating member 20. Once pressed into the hole 28A of the first stop 22, the forward end portion 21A of the penetrating member 20 does not readily come off.

Figure 21:
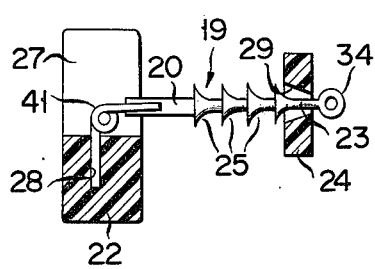
FIG. 21 is a side view of a uterine tube-closing implement according to a third embodiment of the invention, presenting the longitudinal sectional views of the first and second stops.

Unlike the penetrating member of the first and second embodiments, a penetrating member 20 of the third embodiment shown in FIG. 21 has its forward end portion formed of a stainless steel L-shaped spring 41. The free end of the L-shaped spring 41 is inserted into a vertial hole 28 formed in a first stop 22. The forward end portion of the L-shaped spring 41 has the same function as the forward end portions 21, 21A of the first and second embodiments respectively.

Figure 22:
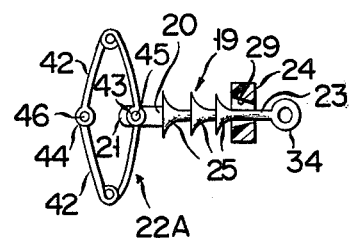
FIG. 22 is a side view of a uterine tube-closing implement according to a fourth embodiment of the invention, showing the longitudinal sectional views of the first and second stops.
Figure 23:
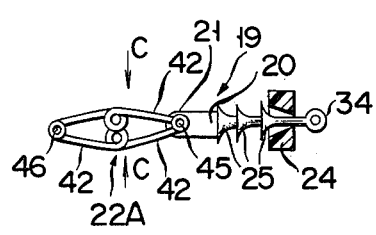
FIG. 23 shows the action of the first stop of FIG. 22.

Reference numeral 22A of FIGS. 22 and 23 denotes a first stop according to a fourth embodiment of the invention. The first stop 22A is formed of a pair of V-shaped springs 42 set in opposite directions so as to collectively form a lozenge.

Each of the V-shaped springs 42 is provided with rings 43, 44 at both ends. The other of the V-shaped springs is similarly provided with rings 43, 44 at both ends. In this case, the same ends are provided with the same rings. The rings 43 are pivoted to the forward end portion 21 of the penetrating member 20 by means of a pin 45. The rings 44 are connected together by a pin 46.

When left free, the first stop 22A extends perpendicularly to the penetrating member 20 to contact the uterine tube 39 over a broader area, thereby effectively closing the uterine tube 39.

When the closing member 19 is pulled back into the needle 2, the inner face of the needle 2 applies to the first stop 22A a force acting in the opposite directions to each other indicated by the arrows C of FIG. 23. As a result, the first stop 22A is flattened as illustrated in FIG. 23, offering the advantage of making it unnecessary to broaden the diameter of the needle 2.

Figure 24:
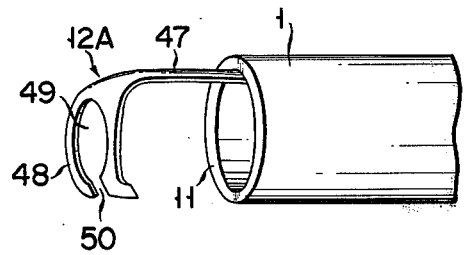
FIG. 24 is an oblique view of the forceps member according to a fifth embodiment of the invention.
Figure 25:
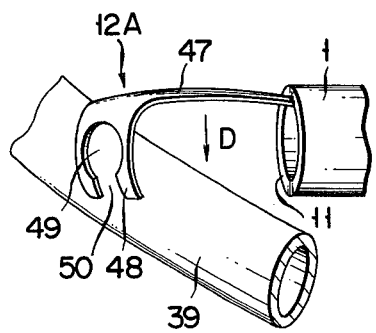
FIG. 25 indicates the state in which the forceps member of FIG. 24 is holding the uterine tube.
Figure 26:
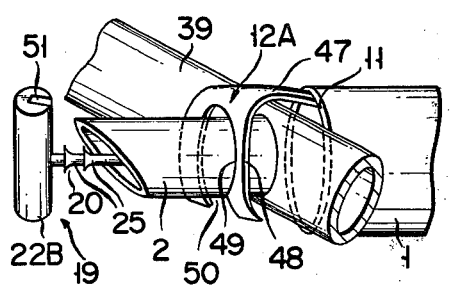
FIG. 26 shows the state in which the uterine tube is being closed by the forceps member of FIG. 24.

FIGS. 24 to 26 show a forceps according to a fifth embodiment of this invention. The forceps 12A comprises a stem 47 and a hook section 48 protruding from the distal end 11 of an outer tube 1 and radially extending inward of the outer tube 1. The hook section 48 has a circular opening 49 which is formed at its center and made large enough to allow for the passage of the needle 2, and a notch 50 contiguous to the opening 49 and the free edge of the hook section 48 to form a pair of prongs. The remaining portions of the forceps 12A have the same construction as those of the forceps members 14 of FIG. 1.

The hook section 48 of the forceps 12A is pushed fully out of the distal end 11 of the outer tube 1 to be set, as shown in FIG. 25, beyond the uterine tube 39 which is going to be closed. The stem 47 of the hook section 48 is moved in the direction of an arrow D indicated in FIG. 25 to let the uterine tube 39 be hold by the hook section 48. The closing implement 19 is pushed, and the subsequent steps are carried out substantially in the same manner as described above to close the uterine tube 39. FIG. 26 illustrates the interim state of the uterine tube-closing operation where the closing implement 19 is pushed out of the needle 2. As shown in FIG. 26, a long groove 51 may be formed in place of a slit in a first stop 22B so as to extend from one end of the first stop 22B to the middle portion thereof. This long groove 51 has the same function as the slit 27 of the first stop of FIGS. 2, 3, 5, 13 to 17, 18, 19 and 21.

What is claimed is:

1. A device for operating a coeliac tubular member-closing implement comprising:

an elongated outer tube having two ends;
a hollow cylindrical needle reciprocably inserted into said outer tube and having two ends, one end thereof being obliquely cut off to provide a sharp tip and containing a coeliac tubular member-closing implement comprising a penetrating member having two ends and a plurality of linearly connected frustoconical engagement members formed between said two ends of said penetrating member with a diameter progressively increasing toward said one end of said needle, a first stop fixed to one end of said penetrating member which is nearer to said one end of said needle and a second stop having a frustoconical bore complementary to said engagement members and allowing for passage of the other end of said penetrating member and the other end of said needle being adapted to project from one end of said outer tube;
a coeliac tubular member-holding forceps extending lengthwise of said outer tube between said outer tube and said needle and having two ends, one end thereof being operated to reciprocate said forceps for allowing the other end thereof to project from, and recede into said one end of said needle;
a push tube reciprocably inserted into said needle for pushing said first stop of said coeliac tubular member-closing implement out of said one end of said needle;
a drive tube reciprocably inserted into said push tube for moving said second stop of said coeliac tubular member-closing implement toward said first stop thereof; and
an elongated holding member for holding said coeliac tubular member-closing implement, said holding member extending through said drive tube and having two ends, one end thereof being detachably connected to the other end of said penetrating member of said coeliac tubular member-closing implement and the other end thereof being adapted to project from said one end of said outer tube.

2. The device according to claim 1 wherein said forceps comprises a pair of forceps members; and each of the forceps members comprises a stem section extending lengthwise of said outer tube between said outer tube and said needle and a coeliac tubular member-holding hook section extending inward radially of said outer tube at said one end thereof and urged outwardly radially of said outer tube.

3. The device according to claim 2 wherein said hook section of each of said forceps members comprises two prongs spaced from each other at an internal large enough to allow for passage of said needle.

4. The device according to claim 1, wherein said forceps comprises a stem section extending lengthwise of said outer tube between said outer tube and said needle and a hook section extending inward radially of said outer tube at said one end thereof and having formed a hole large enough to allow for passage of said needle.

* * * * *